(12) United States Patent
Takeuchi et al.

(10) Patent No.: US 8,513,165 B2
(45) Date of Patent: Aug. 20, 2013

(54) PLANAR LIPID BILAYER ARRAY FORMED BY MICROFLUIDIC TECHNIQUE AND METHOD OF ANALYSIS USING PLANAR LIPID BILAYER

(75) Inventors: Shoji Takeuchi, Tokyo (JP); Hiroaki Suzuki, Tokyo (JP); Sadao Ota, Tokyo (JP); Wei-Heong Tan, Tokyo (JP)

(73) Assignee: The University of Tokyo, Tokyo (JP)

( * ) Notice: Subject to any disclaimer, the term of this patent is extended or adjusted under 35 U.S.C. 154(b) by 271 days.

(21) Appl. No.: 12/744,794

(22) PCT Filed: Nov. 26, 2008

(86) PCT No.: PCT/JP2008/071368
§ 371 (c)(1),
(2), (4) Date: Jul. 9, 2010

(87) PCT Pub. No.: WO2009/069608
PCT Pub. Date: Jun. 4, 2009

(65) Prior Publication Data
US 2010/0304980 A1 Dec. 2, 2010

(30) Foreign Application Priority Data

Nov. 26, 2007 (JP) ................................. 2007-304126

(51) Int. Cl.
*C40B 60/00* (2006.01)
*C12M 1/34* (2006.01)
(52) U.S. Cl.
USPC ........................... 506/33; 435/287.1; 436/172

(58) Field of Classification Search
None
See application file for complete search history.

(56) References Cited

U.S. PATENT DOCUMENTS

| 6,124,138 A * | 9/2000 | Woudenberg et al. ........ 436/518 |
| 2005/0230272 A1* | 10/2005 | Lee et al. ...................... 205/792 |

FOREIGN PATENT DOCUMENTS

JP 2006-312141 11/2006

OTHER PUBLICATIONS

Randall et al. (Proc. Natl. Acad. Sci., 2005, 102:10813-10818).*
Suzuki et al, "Three-Dimensional Micro Fluidic Chip for Membrane Protein Analysis Fabricated by Stereolithography", The Institute of Electrical Engineers of Japan Bio Microsystem Kenkyukai Shiryo, Jul. 2, 2007, vol. BMS-07-7-31, pp. 1 to 4, abstract only.

(Continued)

*Primary Examiner* — Ardin Marschel
*Assistant Examiner* — Jeremy C Flinders
(74) *Attorney, Agent, or Firm* — Bacon & Thomas, PLLC

(57) ABSTRACT

There is provided a planar lipid bilayer array formed by microfluidic technique and a method of analysis using the planar lipid bilayers, providing the advantages such as portability, decreased analysis time, a smaller amount of required reagents, and parallel automation with high reproducibility. The planar lipid bilayer array formed by microfluidic technique is a planar lipid bilayer array formed by microfluidic technique (PDMS device) 1 saturated with water by preliminarily immersing in water, comprising microchannels 2 connected to an inlet of a microfluidic channel and arranged in parallel, and microchambers 3 having apertures on both sides of the microchannel 2.

3 Claims, 5 Drawing Sheets

(56) References Cited

OTHER PUBLICATIONS

Kuribayashi et al., "Formation of monodisperse Giant Liposomes in Microfluidic Channel", The Institute of Electrical Engineers of Japan Bio Microsystem Kenkyukai Shiryo, 2006, vol. BMS-06-1-14, pp. 47 to 50, abstract only.

Kang, et al., "A Storable Encapsulated Bilayer Chip Containing a Single Protein Nanopore", J. Am. Chem. Soc., Apr. 18, 2007, vol. 129, No. 15, pp. 4701 to 4705.

Zhu et al., "Global Analysis of Protein Activities using Proteome Chips", Science, vol. 293, pp. 2101-2105, 2001.

Alberts et al., "Molecular Biology of the Cell"; 4th Edition, Garland Science, 2002, pp. 680-683.

Ide et al., "An Artificial Lipid Bilayer Formed on an Agarose CoatedGlass for Simultaneous Electrical and optical Measurement of Sinle Ion Channels", Biochem. Biophys Res. Comm., 265, pp. 595-599, 1999.

Malmstadt et al., "Automated Formation of Lipid-Bilayer Membranes in a Microfluidic Device", Nano Lett., vol. 6, No. 9, pp. 1961-1965, 2006.

Mayer et al., Microfabricated Teflon Membranes for Low-Noise Recordings of Ion Channels in Planar Lipid Bilayers, BioPhys., vol. 85, pp. 2684-2695, 2003.

Hemmler et al., "Nanopore Unitary Permeability Measured by Electrochemical and Optical Single Transporter Recording", Biophys., vol. 88, pp. 4000-4007, 2005.

* cited by examiner

PLANAR LIPID BILAYER ARRAY FORMED BY MICROFLUIDIC TECHNIQUE AND METHOD OF ANALYSIS USING PLANAR LIPID BILAYER

TECHNICAL FIELD

The present invention relates to a planar lipid bilayer array formed by microfluidic technique and a method of analysis using the planar lipid bilayers, and in particular, to a planar lipid bilayer array formed by microfluidic technique for membrane protein analysis and a method of analysis of the membrane proteins using the same.

BACKGROUND ART

With the growing number of sequenced genomes, there has been a greater opportunity for proteome research (see Non-Patent Document 1). After the success of the DNA array chips which brought a revolution in genome researches, the "protein array chips" that are capable of high-throughput analysis of the expression and interaction of proteins are greatly sought after (see Non-Patent Document 2). Specifically, studies focusing on the functionality of membrane proteins are important since they are vital in regulating the transport of various molecules in and out of cells.

However, handling membrane proteins such as ion channels, pumps, receptors, and transporters has been challenging as they only function when embedded in a lipid layer, i.e., a fundamental structure of all bio-membranes (see Non-Patent Document 3). As a result, the primary targets of most protein chips have been mostly water-soluble proteins.

Patch clamping (see Non-Patent Document 4) and artificial lipid bilayer (see Non-Patent Document 5) experiments have been two major established methods in the fundamental studies of membrane proteins. However, both methods require the experienced skills to perform and have not realized good reproducibility due to a lack of high-throughput operations. Recently, several research groups have tried to overcome these problems by working on generating planar bilayers in microfluidic devices (see Non-Patent Documents 6-8). Integrated microfluidic systems offer a vast array with advantages including portability, decreased analysis time, a smaller amount of required reagents, and parallel automation with high reproducibility. Although realizing these benefits leads to the high-throughput and quantitative measurements for analyzing membrane transport, such simple techniques or devices have not existed yet.

Non-Patent Document 1: V. Santoni, M. Molley, T. Rabillound, "Membrane proteins and proteomics: Un amour impossible?", Electrophoresis, 21, 1054-1070, 2000

Non-Patent Document 2: H. Zhu, M. Bilgin, R. Bangham, David Hall, Antonio Casamayor, P. Bertone, N. Lan, R. Jansen, S. Bidlingmaier, T. Houfek, T. Mitchell, P. Miller, R. A. Dean, M. Gerstein, and M. Snyder, "Global Analysis of Protein Activities using Proteome Chips", Science., Vol. 293, 2101-2105, 2001

Non-Patent Document 3: M. Bloom, E. Evans, O. G. Mouritsen, "Physical Properties of the Fluid Lipid-Bilayer Component of Cell Membranes: a Perspective", Q. Rev. Biophys., Aug.; 24(3), 293-397, 1991

Non-Patent Document 4: B. Alberts et al., "Molecular Biology of the Cell; 4th Ed.,", Garland Science, 2002

Non-Patent Document 5: T. Ide, and T. Yanagida, "An Artificial Lipid Bilayer Formed on an Agarose Coated Glass for Simultaneous Electrical and Optical Measurement of Single Ion Channels", Biochem. Biophys. Res. Comm., 265, pp. 595-599, 1999

Non-Patent Document 6: R. Hemmier, G. Bose, E. Wagner, and R. Peters, "Nanopore Unitary Permeability Measured by Electrochemical and Optical Single Transporter Recording", Biophys., Vol. 88, 4000-4007, 2005

Non-Patent Document 7: N. Malmstadt, M. A. Nash, R. F. Purnell, and J. J. Schmidt, "Automated Formation of Lipid-Bilayer Membranes in a Microfluidic Device", Nano Lett., Vol. 6, No. 9, 1961-1965, 2006

Non-Patent Document 8: M. Mayer, J. K. Kriebel, M. T. Tosteson, and G. M. Whitesides "Microfabricated Teflon Membranes for Low-Noise Recordings of Ion Channels in Planar Lipid Bilayers", BioPhys., Vol. 85, 2684-2695, 2003

SUMMARY OF THE INVENTION

As described above, a simple method and a device for the same having the above-mentioned advantages have not existed yet.

In view of the above-described problems, the present invention is intended to provide a planar lipid bilayer array formed by microfluidic technique and a method of analysis using the planar lipid bilayers having the advantages such as portability, decreased analysis time, a smaller amount of required reagents, and parallel automation with high reproducibility.

In order to achieve the object described above, the present invention provides the following:

[1] A planar lipid bilayer array formed by microfluidic technique, wherein the planar lipid bilayer array comprises: (i) microchannels connected to an inlet of a microfluidic channel and arranged in parallel; and (ii) microchambers having apertures on both sides of the microchannel.

[2] The planar lipid bilayer array formed by microfluidic technique according to [1], wherein the apertures on the both sides of the microchannel are arranged in a zigzag manner in relation to the microchannel.

[3] The planar lipid bilayer array formed by microfluidic technique according to [1], wherein the planar lipid bilayer array is an array saturated with water by preliminarily immersing in water.

[4] The planar lipid bilayer array formed by microfluidic technique according [3], wherein the array is configured by PDMS.

[5] The planar lipid bilayer array formed by microfluidic technique according to [1], wherein the both sides of the microchannel are both sidewalls of the microchannel.

[6] The planar lipid bilayer array formed by microfluidic technique according to [1], wherein the both sides of the microchannel are top and bottom walls of the microchannel.

[7] The planar lipid bilayer array formed by microfluidic technique according to [1], wherein the microchannel is 7 μm in height, and the microchamber is 17 μm in width and 19 μm in height.

[8] The planar lipid bilayer array formed by microfluidic technique according to [1], comprising a single microsyringe and a single tube connected to the microsyringe, wherein a buffer solution containing membrane protein and fluorescent material, an organic solvent containing lipid, and a buffer solution containing no dissolved materials are infused sequentially into the tube from the tip, and the tip of the tube is connected to the inlet of the microfluidic channel.

[9] A method of analysis using planar lipid bilayers, comprising the steps of: preliminarily immersing a planar lipid bilayer array formed by microfluidic technique in water to saturate with water; and with the use of microchannels arranged in parallel in the planar lipid bilayer array saturated with water and microchambers having apertures on both sides of the microchannel, forming the planar lipid bilayers in the apertures to seal the microchambers.

[10] The method of analysis using planar lipid bilayers according to [9], wherein the apertures on the both sides of the microchannels are arranged in a zigzag manner in relation to the microchannels.

[11] The method of analysis using planar lipid bilayers according to [9], comprising the steps of: infusing a buffer solution containing membrane protein and fluorescent material into the microchannels and the microchambers; infusing an organic solvent containing lipid into the microchannels; and infusing a buffer solution containing no dissolved materials into the microchannels.

[12] The method of analysis using planar lipid bilayers according to [11], wherein the membrane protein is α-Hemolysin, the fluorescent material is Calcein, the lipid is phosphatidycoline (PC), and the organic solvent is hexadecane.

[13] The method of analysis using planar lipid bilayers according to [11], wherein the membrane protein is α-Hemolysin, the fluorescent material is Calcein, the lipid is phosphatidycoline (PC), and the organic solvent is squalene.

[14] A method of analysis using planar lipid bilayers, wherein a degree of membrane transport of the planar lipid bilayer is measured by deforming the planar lipid bilayer fabricated according to [11], forming a liposome, and introducing Hemolysin into the liposome.

[15] The method of analysis using the planar lipid bilayers according to [14], wherein a degree of decrease in the fluorescence intensity is measured in the liposome containing fluorescent material in addition to Hemolysin.

DESCRIPTION OF THE PREFERRED EMBODIMENTS

A planar lipid bilayer array formed by microfluidic technique according to the present invention is the planar lipid bilayer array formed by microfluidic technique saturated with water by preliminarily immersing in water, comprising microchannels connected to an inlet of a microfluidic channel and arranged in parallel, and microchambers having apertures on both sides of the microchannel.

Embodiments

Hereinbelow, embodiments of the present invention will be described in detail.

Figure 1:
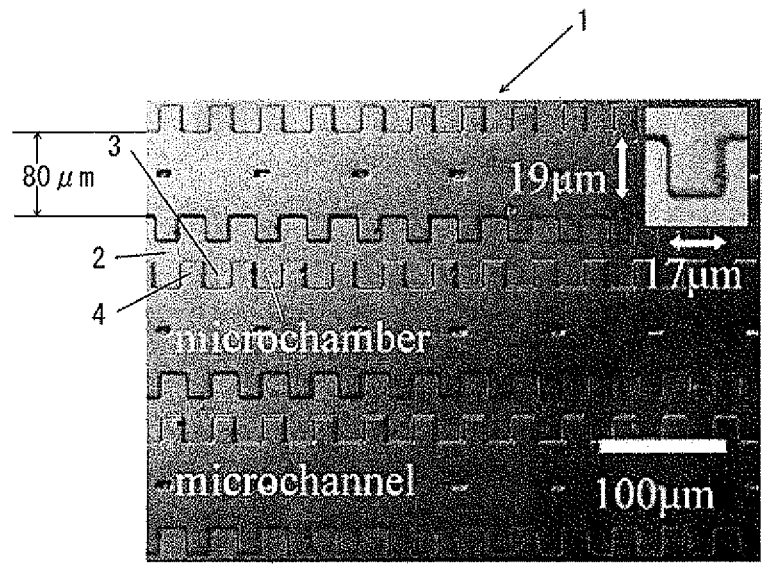
FIG. 1 is a conceptual diagram of microchannels having microchambers of a PDMS device illustrating an embodiment of the present invention.
Figure 2:
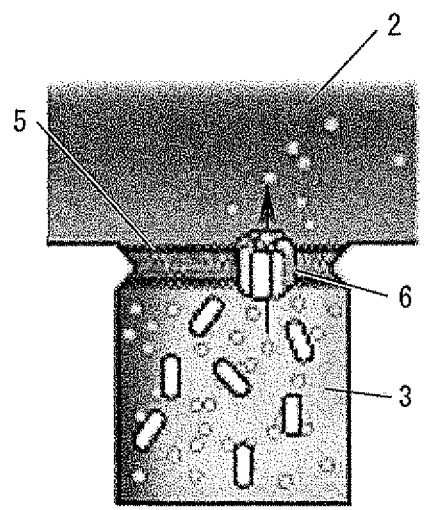
FIG. 2 is a diagram showing the microchamber sealed with a planar lipid bilayer illustrating the embodiment of the present invention.

FIG. 1 is a conceptual diagram of microchannels having microchambers of a PDMS device illustrating an embodiment of the present invention. FIG. 2 is a diagram showing the microchamber sealed with a planar lipid bilayer.

In these figures, reference numeral 1 denotes a PDMS (Polydimethylsiloxane) device, 2 denotes a microchannel formed in the PDMS device 1, and 3 denotes a microchamber having an aperture alternately arranged on both sides of the microchannel 2. Although the both sides of the microchannel 2 are exemplified as side walls of the microchannel herein, the both sides of the microchannel 2 may refer to top and bottom walls of the microchannel. Here, each microchannel 2 is 7 μm in height, and the size of each microchamber 3 is 17 μm in width and 19 μm in height, for example.

Here, although the smaller membrane area of a planar lipid bilayer 5 formed on the aperture of the microchamber 3 aids the stability of itself, as described later, the excess specific area may cause a problem that the PDMS device 1 swells significantly by absorbing an organic solvent. For example, in the case of the microchamber 3 with the width of 7 μm, the microchamber 3 was closed due to the swelling mentioned above. Also with the width of 10 μm, the microchamber 3 was deformed, which obstructed the formation of the planar lipid bilayer. Accordingly, the microchamber 3 was optimized to have the width of 17 μm.

In addition, in order to stabilize the planar lipid bilayer 5, the height of the microchannel 2 is as small as 7 μm compared to the spacing of 80 μm between the microchannels 2, resulting in a problem that the PDMS device 1 structurally collapses. For solving this problem, the microchambers having the apertures are alternately arranged on the both sides of the microchannel 2, so that PDMS pillars 4 are aligned in the middle of the main microchannels, imparting a robust structure to the PDMS device 1 to prevent the microchannels from structurally collapsing.

Moreover, the PDMS device 1 can set a vast number of microchambers arranged in parallel.

Further, the aperture of each microchamber 3 is sealed with the planar lipid bilayer 5, and the transport of fluorescent molecules through a nanopore 6 (formed when α-Hemolysin monomers heptamerize) present in the planar lipid bilayer 5 is measured as a change in the fluorescent density under a fluorescent microscope.

Here, while PDMS is the preferred material for the array described above, it is not limited thereto and inorganic or plastic materials such as glass, SU-8, silicon, acrylic resin, and PET may be used.

This device can attain portability, decreased analysis time, a smaller amount of required reagents, and parallel automation with high reproducibility.

Figure 3:
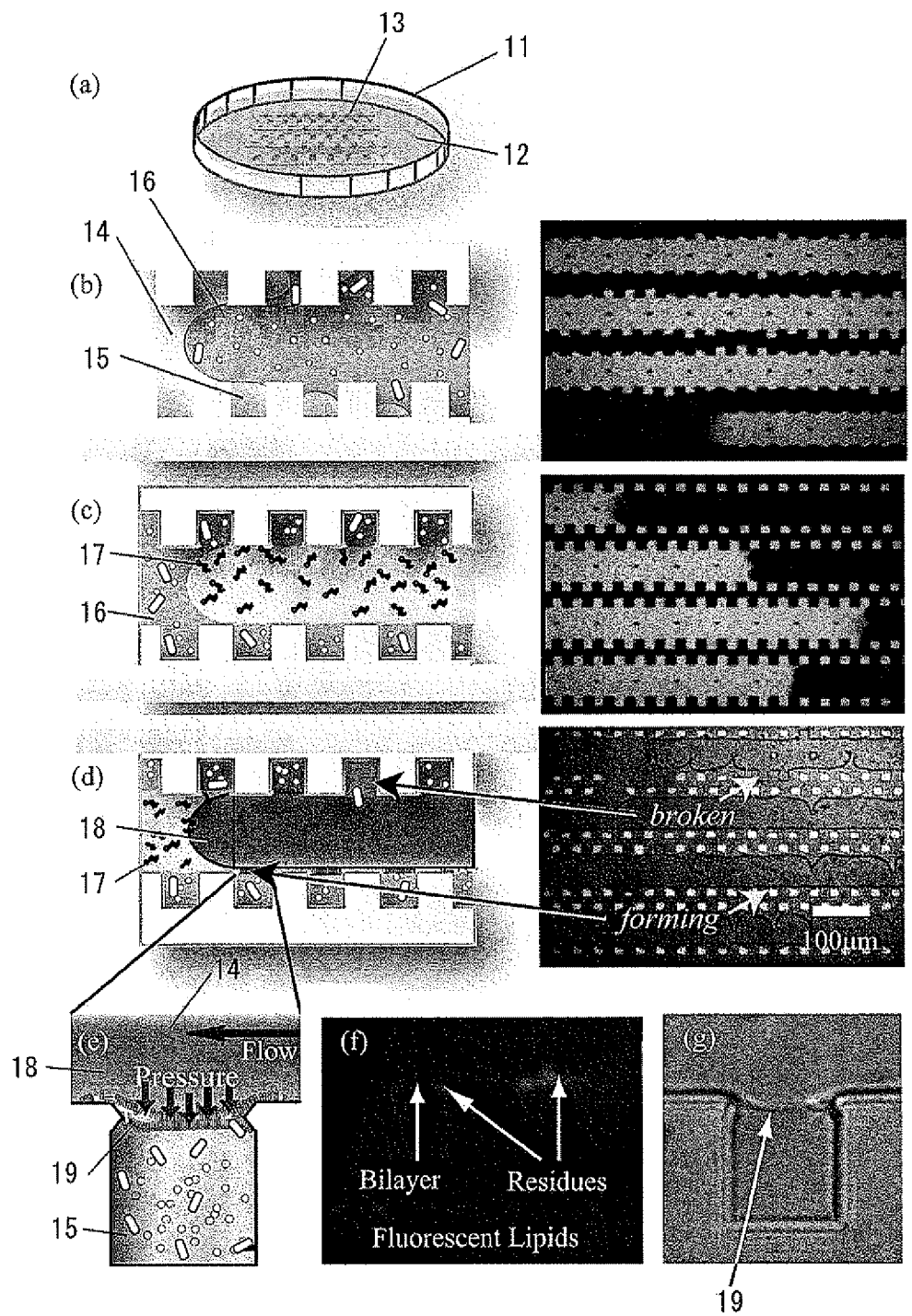
FIG. 3 is a diagram showing a method of forming the planar lipid bilayer in the microchamber illustrating the embodiment of the present invention.

FIG. 3 is a diagram showing a method of forming the planar lipid bilayer in the microchamber illustrating the embodiment of the present invention, wherein FIG. 3(a) shows the saturation of the PDMS device with water by immersion; FIG. 3(b) shows the infusion of a buffer solution containing membrane protein (α-Hemolysin) and fluorescent material (Calcein); FIG. 3(c) shows the infusion of a lipid solution (organic solvent (hexadecane) containing phosphatidycoline (PC)); FIG. 3(d) shows the infusion (flushing) of the microchannels with a buffer solution containing no dissolved materials; FIGS. 3(e) and (f) show the microchambers with the planar lipid bilayer formed therein; and FIG. 3(g) shows an enlarged view of the lipid bilayer formed in the microchamber. Here, the organic solvent, hexadecane, mentioned above can be replaced by another organic solvent, squalene, to extend the applications.

First, as shown in FIG. 3(a), a PDMS device 13 is saturated with water by immersing in water 12 in a petri dish 11 for 12 hours or more. This is for preventing water from absorbing into the PDMS device 13 during the operation. Next, as shown in FIG. 3(b), a phosphate buffer solution 16 containing membrane protein ($\alpha$-Hemolysin) and fluorescent material (Calcein) is infused into microchannels 14 and microchambers 15 of the PDMS device 13 saturated with water. Next, as shown in FIG. 3(c), a lipid solution (organic solvent (hexadecane) containing phosphatidycoline (PC)) 17 is infused into the microchambers 15 loaded with the phosphate buffer solution 16. Next, as shown in FIG. 3(d), a buffer solution 18 containing no dissolved materials is infused into the microchannels 14. Thereby, as shown in FIGS. 3(e) and (f), due to the flow of the buffer solution 18 and the absorption of the organic solvent into the PDMS device, the organic solvent covering the microchambers 15 thins down, and the aperture of the microchamber 15 is sealed with a planar lipid bilayer 19. Note that FIG. 3(d) also shows the broken planar lipid bilayers.

In this manner, according to the present invention, the planar lipid bilayers 19 are readily fabricated, that allows for rapid and accurate analyses of the membrane proteins.

Figure 4:
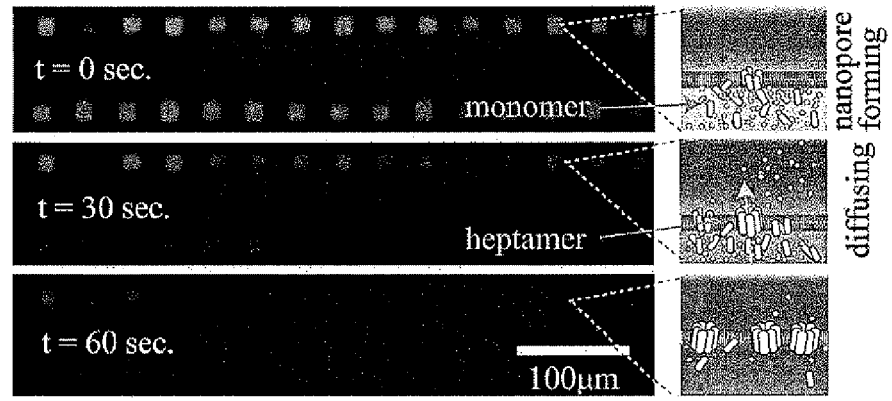
FIG. 4 is a diagram showing a process of rapid decrease in the fluorescent intensity in the microchamber due to the diffusion of fluorescent material (Calcein) into the microchannel through nanopores formed by membrane protein (α-Hemolysin) illustrating the embodiment of the present invention.

FIG. 4 is a diagram showing a process of rapid decrease in the fluorescent intensity in the microchamber due to the diffusion of the fluorescent material (Calcein) into the microchannel through nanopores formed by the membrane protein ($\alpha$-Hemolysin) illustrating the embodiment of the present invention.

Figure 5:
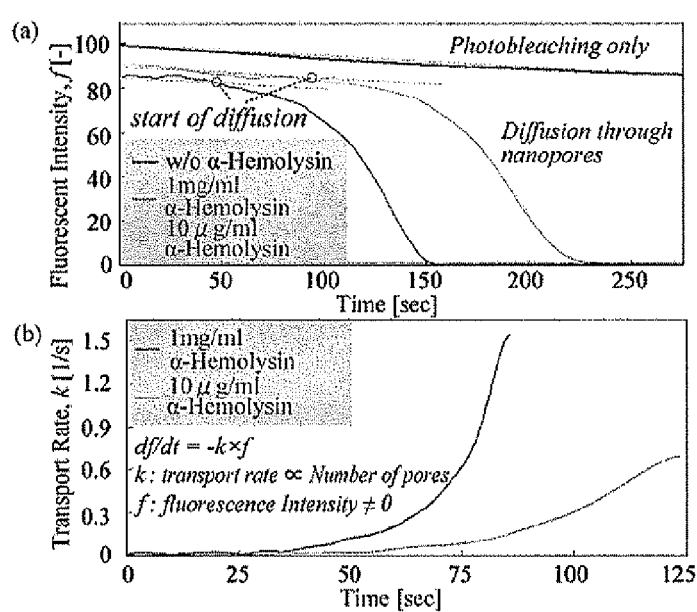
FIG. 5 is a diagram showing characteristics of a change in the fluorescent intensity in the microchambers illustrating the embodiment of the present invention.

FIG. 5(a) is a diagram showing a progress of the fluorescent intensity in the microchambers. As can be seen, without the membrane protein ($\alpha$-Hemolysin), the decrease in the fluorescent intensity is only due to photobleaching. On the other hand, with the membrane protein ($\alpha$-Hemolysin), the rapid decrease can be observed due to the diffusion of the fluorescent material from the nanopores formed.

FIG. 5(b) is a diagram showing a transport rate k calculated based on FIG. 5(a). Here, (df/dt=−kf), i.e., the transport rate k is proportional to the number of membrane protein ($\alpha$-Hemolysin) contained.

In this manner, the membrane proteins such as ion channels, pumps, receptors, and transporters can be manipulated.

Figure 6:
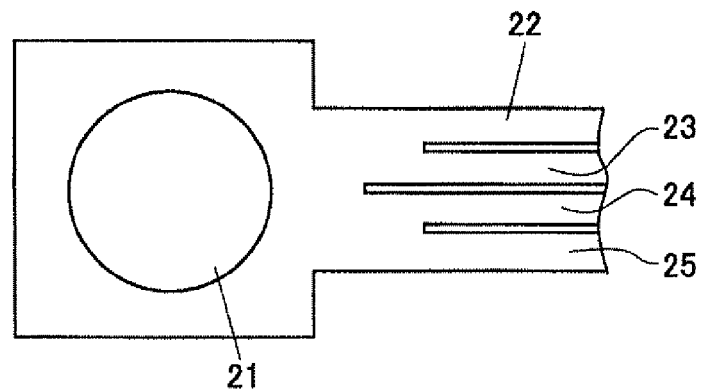
FIG. 6 is a schematic diagram showing a structure running from an inlet of a microfluidic channel to a planar lipid bilayer array formed by microfluidic technique (PDMS device) illustrating the embodiment of the present invention.
Figure 7:
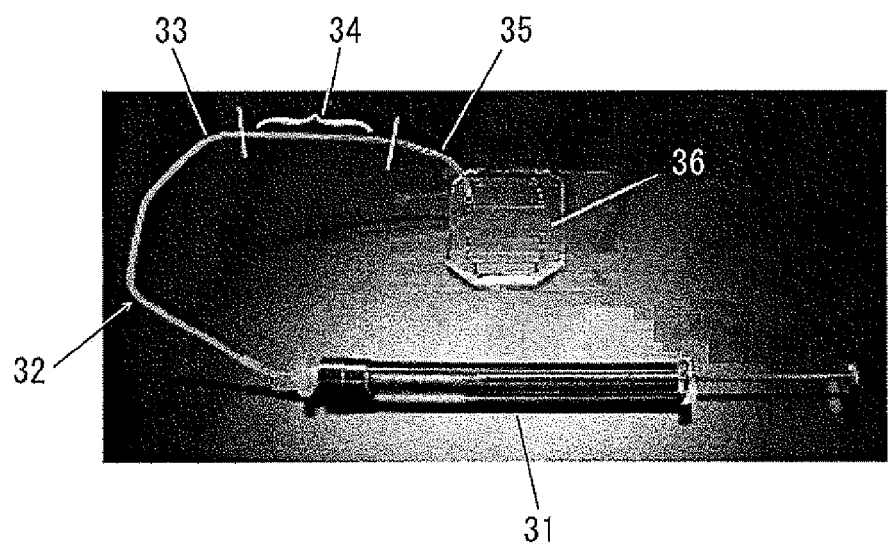
FIG. 7 is a diagram showing an experimental system of the present invention.

FIG. 6 is a schematic diagram showing a structure running from an inlet of a microfluidic channel to the planar lipid bilayer array formed by microfluidic technique (PDMS device) illustrating the embodiment of the present invention, and FIG. 7 is a diagram showing an experimental system.

When a flow rate of the buffer solution 18 containing no dissolved materials, shown in FIG. 3, is high, it causes the problem that membranes of the organic solvent containing lipid (lipid solution 17) remaining in the apertures of the microchambers experience an excess dynamic stress due to the flow of the buffer solution 18, resulting in the breakage of the planar lipid bilayer before fabrication. In order to prevent this, as shown in FIG. 6, flow paths 22, 23, 24, and 25 for infusing liquid from an inlet of a microfluidic channel 21 are parallelized to allow for liquid feeding at low rate. With the decrease in the flow rate, the dynamic stress is decreased which is applied by the flow of the buffer solution 18 to the membranes of the organic solvent containing lipid. Thereby, the probability of the planar lipid bilayers to be broken before fabrication can be reduced.

Next, an experiment system will be described.

In performing the method of fabricating the planar lipid bilayer according to the present invention, the buffer solution/lipid solution/buffer solution containing no dissolved materials must be fed separately and sequentially into the microchannels. However, there has been a problem that, if syringes are exchanged per solution, a large quantity of micellar contamination is introduced due to the entrapment of air or the like.

In the present invention, each process can be performed without air entrapment between the solutions by using a single syringe to sequentially load a single tube with the solutions.

Note that although a syringe is preferred for liquid feeding in the above embodiment, it is not limited thereto and the liquid feeding can be performed manually by using other tools such as a pump or a pipette.

In FIG. 7, reference numeral 31 denotes a microsyringe, and 32 denotes a tube connected to the microsyringe 31. The tube 32 is loaded with a buffer solution 33 containing no dissolved materials, a lipid solution 34, and a phosphate buffer solution 35 containing the fluorescent material (Calcein) and the membrane protein ($\alpha$-Hemolysin). Reference numeral 36 denotes a PDMS (Polydimethylsiloxane) device (planar lipid bilayer array for membrane protein analysis) described above.

By configuring in this manner, the liquid including the phosphate buffer solution 35/lipid solution 34/buffer solution 33 containing no dissolved materials can be loaded sequentially into the single tube 32 using the single microsyringe 31, and the process of fabricating the planar lipid bilayer can be performed without air entrapment between the solutions.

Figure 8:
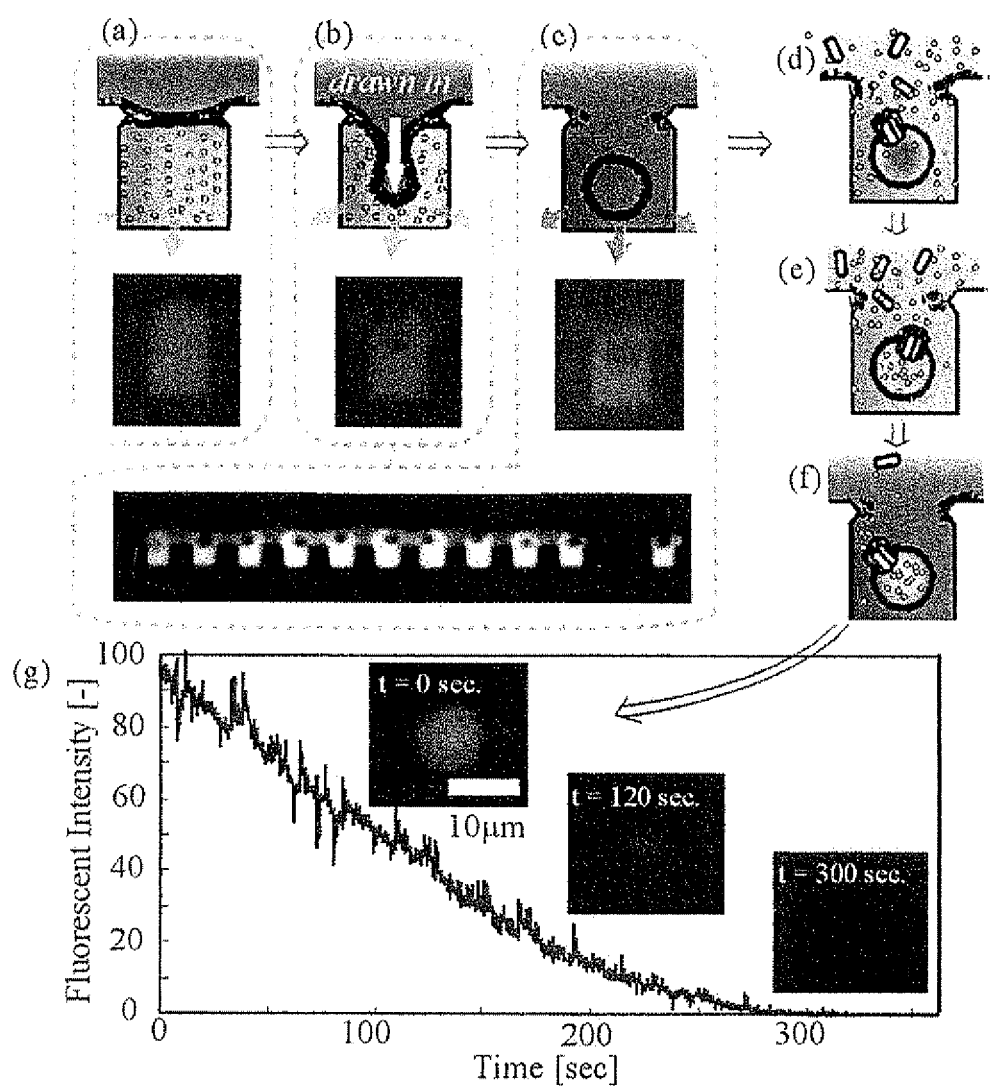
FIG. 8 is a diagram showing a process of measurement of membrane transport by the formation of a liposome using the planar lipid bilayer of the present invention.

FIG. 8 is a diagram showing a process of measurement of membrane transport by the formation of liposomes using the planar lipid bilayer of the present invention.

First, the PDMS saturated with water is left in the ambient air for several hours, and then, as shown in FIG. 8(a), the planar lipid bilayer is formed without containing $\alpha$-Hemolysin. Next, as shown in FIG. 8(b), as the buffer solution is absorbed into the PDMS, the planar lipid bilayer is drawn into the chamber, resulting in a liposome as shown in FIG. 8(c). As shown in FIG. 8(d), as the buffer solution containing $\alpha$-Hemolysin and Calcein (fluorescent material) is introduced, Calcein is diffused into the liposome, as shown in FIG. 8(e). As shown in FIG. 8(f), as the external solutions are exchanged, Calcein is diffused out of the liposome through $\alpha$-Hemolysin. This phenomenon can be observed, as shown in FIG. 8(g), from the decrease in the fluorescent intensity in the liposome.

In this manner, the degree of membrane transport of the planar lipid bilayer can be measured by deforming the planar lipid bilayer fabricated according to the above-described method, forming the liposome, and introducing Hemolysin into the liposome.

Thereby, the membrane proteins can be analyzed.

According to the present invention, as described above:

(1) In order to prevent water from being absorbed into the PDMS during the operation, the PDMS device (lipid bilayer array) is immersed in water for 12 hours or more to saturate with water.

(2) By sequentially infusing the phosphate buffer solution/lipid solution/buffer solution containing no dissolved materials into the microchannels having a vast number of microchambers, the lipid bilayer can be easily formed, and each microchamber is sealed with the planar lipid bilayer containing the membrane protein. Since the microchamber (2 pl) has a small volume, the membrane transport of fluorescent molecules can be observed by well observing a change in the fluorescent intensity. That is, the transport of the fluorescent material (Calcein) through the nanopores formed by the membrane protein (α-Hemolysin) can be well measured quantitatively.

In addition, the quantitative analysis experiments of the membrane proteins are realized at a monomolecular level.

That is, the high integration of the microchambers arrayed with high density along the parallel microchannels allows for measurements of a large number of microchambers in a single field of view (176 chambers with a 20× optical lens), which enables a vast number of the quantitative biochemical experimental analyses.

Moreover, utilizing the microchambers enables the accurate detection because the activity of the membrane proteins at a monomolecular level brings a significant change in parameters (change in the fluorescent luminance) of the system.

Here, measurements can be performed without using the membrane proteins by extending the planar lipid bilayer. For example, the planar lipid bilayer containing fluorescent molecules can be utilized to measure a degree of environmental contamination by analyzing luminance of the fluorescent molecules. Even without the membrane proteins, using a temperature-responsive planar lipid bilayer enables regulation of materials to allow or prevent penetration therethrough.

In addition, the present invention should not be limited to the embodiments described above, and a number of variations are possible on the basis of the spirit of the present invention. These variations should not be excluded from the scope of the present invention.

According to the present invention, the following effects can be achieved.

(1) The advantages are achieved such as portability, decreased analysis time, a smaller amount of required reagents, and parallel automation with high reproducibility.

(2) A vast number of microchambers arranged in parallel can be set, that allows for rapid and accurate analyses of the membrane proteins.

INDUSTRIAL APPLICABILITY

The planar lipid bilayer array formed by microfluidic technique for membrane protein analysis according to the present invention is applicable to the analysis of membrane proteins by incorporating a vast number of microchambers arranged in parallel.

The invention claimed is:
1. A planar lipid bilayer array formed by microfluidic technique on a polydimethylsiloxane substrate saturated with water, wherein the polydimethylsiloxane substrate comprises:
  (i) microchannels connected to an inlet of a microfluidic channel, and arranged in parallel; and
  (ii) microchambers having apertures providing fluid communication with a microchannel, the microchambers being located on both sides of each of the microchannels; and
  wherein the apertures of the microchambers are sealed with a planar lipid layer; and
  wherein each of the microchannels is located between opposing walls of the substrate and apertures of the microchambers are located in both of the opposing walls of the substrate.

2. The planar lipid bilayer array formed by microfluidic technique according to claim 1, wherein the apertures on the both sides of the microchannel are arranged in a zigzag manner in relation to the microchannel.

3. The planar lipid bilayer array formed by microfluidic technique according to claim 1, wherein the microchannel is 7 μm in height, and the microchamber is 17 μm in width and 19 μm in height.

* * * * *